US009724182B2

(12) United States Patent
Taylor

(10) Patent No.: US 9,724,182 B2
(45) Date of Patent: Aug. 8, 2017

(54) CONNECTOR CUFF

(71) Applicant: Coloplast A/S, Humlebaek (DK)

(72) Inventor: Jeffrey Brian Taylor, Forest Lake, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/521,475

(22) Filed: Oct. 23, 2014

(65) Prior Publication Data

US 2016/0106527 A1    Apr. 21, 2016

Related U.S. Application Data

(60) Provisional application No. 62/065,011, filed on Oct. 17, 2014.

(51) Int. Cl.
A61F 2/00 (2006.01)

(52) U.S. Cl.
CPC ...... *A61F 2/004* (2013.01); *A61F 2220/0033* (2013.01); *A61F 2230/0006* (2013.01); *A61F 2230/0008* (2013.01); *A61F 2250/001* (2013.01); *A61F 2250/0003* (2013.01); *A61F 2250/0013* (2013.01)

(58) Field of Classification Search
CPC ........ F16L 33/227; A61B 39/00; A61F 2/004; A61F 2250/0013; A61F 2220/0033; A61F 2230/0008; A61F 2250/0003; A61F 2230/0006; A61F 2/0036; A61F 2/0054; A61F 2005/415; A61F 5/41; A61F 5/005; A61F 2/0013; A61F 2/0027; A61F 2/2442–2/246; A61F 2/005; Y10S 128/25; A61M 16/008364
See application file for complete search history.

(56) References Cited

U.S. PATENT DOCUMENTS

| 2,455,859 | A | * | 12/1948 | Foley | A61F 2/0054 128/DIG. 25 |
| 3,461,863 | A | * | 8/1969 | Sullinger | A61F 5/41 600/41 |
| 3,744,063 | A | | 7/1973 | McWhorter et al. | |
| 3,863,622 | A | * | 2/1975 | Buuck | A61F 2/004 128/DIG. 25 |
| 4,063,548 | A | | 12/1977 | Klatt et al. | |

(Continued)

FOREIGN PATENT DOCUMENTS

| EP | 0093507 A1 | 11/1983 |
| EP | 1676543 A1 | 7/2006 |

(Continued)

OTHER PUBLICATIONS

American Medical Systems, AMS 800TM Urinary Control System Operating Room Manual, 2004.

*Primary Examiner* — Christine H Matthews
(74) *Attorney, Agent, or Firm* — Coloplast Corp., Coloplast A/S; Nick Baumann

(57) ABSTRACT

An artificial urinary sphincter (AUS) system that includes an elastic tube to be wrapped around a urethra and having at least one connector. The elastic tube has a first end to receive and dispatch fluid and a second end to be connected to the at least one connector. The elastic tube receives and dispatches the fluid to expand and contract the elastic tube and to coapt the urethra for continence and open the urethra for voiding.

18 Claims, 9 Drawing Sheets

(56) References Cited

U.S. PATENT DOCUMENTS

| | | | |
|---|---|---|---|
| 4,191,196 A | 3/1980 | Bradley et al. | |
| 4,222,377 A | 9/1980 | Burton | |
| 4,408,597 A | 10/1983 | Tenney, Jr. | |
| 4,412,530 A | 11/1983 | Burton | |
| 4,428,365 A | 1/1984 | Hakky | |
| 4,517,967 A | 5/1985 | Timm et al. | |
| 4,522,198 A | 6/1985 | Timm et al. | |
| 4,559,931 A | 12/1985 | Fischell | |
| 4,584,900 A * | 4/1986 | Masuda | B29C 70/44 74/552 |
| 4,723,538 A * | 2/1988 | Stewart | A61F 5/41 600/41 |
| 4,724,830 A | 2/1988 | Fischell | |
| 4,727,887 A * | 3/1988 | Haber | A61B 17/12 128/DIG. 25 |
| 4,786,276 A | 11/1988 | Haber | |
| 4,878,889 A | 11/1989 | Polyak | |
| 4,909,785 A | 3/1990 | Burton et al. | |
| 4,932,956 A | 6/1990 | Reddy et al. | |
| 4,932,958 A | 6/1990 | Reddy et al. | |
| 4,994,020 A | 2/1991 | Polyak | |
| 5,027,800 A * | 7/1991 | Rowland | A61F 5/41 600/39 |
| 5,048,511 A | 9/1991 | Rosenbluth et al. | |
| 5,078,720 A | 1/1992 | Burton et al. | |
| 5,254,092 A | 10/1993 | Polyak | |
| 5,335,669 A | 8/1994 | Tihon et al. | |
| 5,356,423 A | 10/1994 | Tihon et al. | |
| 5,366,474 A * | 11/1994 | Blumenkanz | A61F 9/00727 606/202 |
| 5,496,271 A | 3/1996 | Burton et al. | |
| 5,499,994 A | 3/1996 | Tihon et al. | |
| 5,518,504 A | 5/1996 | Polyak | |
| 5,720,415 A | 2/1998 | Morningstar | |
| 5,855,548 A * | 1/1999 | Place | A61F 5/41 128/885 |
| 5,895,356 A | 4/1999 | Andrus et al. | |
| 6,171,233 B1 | 1/2001 | Willard | |
| 6,319,237 B1 | 11/2001 | Krumme | |
| 6,382,214 B1 | 5/2002 | Raz et al. | |
| 6,460,262 B1 | 10/2002 | Cabak et al. | |
| 6,558,315 B1 | 5/2003 | Kuyava | |
| 6,612,977 B2 | 9/2003 | Staskin et al. | |
| 6,616,653 B2 | 9/2003 | Beyar et al. | |
| 6,652,450 B2 | 11/2003 | Neisz et al. | |
| 6,802,807 B2 | 10/2004 | Anderson et al. | |
| 6,971,986 B2 | 12/2005 | Staskin et al. | |
| 6,991,601 B2 | 1/2006 | Kuyava et al. | |
| 7,015,253 B2 | 3/2006 | Escandon et al. | |
| 7,048,682 B2 | 5/2006 | Neisz et al. | |
| 7,083,568 B2 | 8/2006 | Neisz et al. | |
| 7,267,645 B2 | 9/2007 | Anderson et al. | |
| 7,291,104 B2 | 11/2007 | Neisz et al. | |
| 7,315,762 B2 | 1/2008 | Mosher et al. | |
| 7,946,975 B2 | 5/2011 | George et al. | |
| 7,996,092 B2 | 8/2011 | Mrva et al. | |
| 8,062,209 B2 | 11/2011 | Rowland et al. | |
| 8,491,462 B2 | 7/2013 | Chechik | |
| 8,684,910 B2 | 4/2014 | Chechik | |
| 8,740,769 B2 | 6/2014 | Chechik | |
| 2003/0028076 A1 | 2/2003 | Kuyava et al. | |
| 2004/0049209 A1* | 3/2004 | Benchetrit | A61F 5/0066 606/151 |
| 2007/0249893 A1 | 10/2007 | Krumme | |
| 2008/0027483 A1* | 1/2008 | Cartledge | A61B 5/061 606/201 |
| 2012/0101509 A1* | 4/2012 | Paganon | A61F 2/004 606/151 |
| 2012/0108892 A1 | 5/2012 | Beckman et al. | |
| 2013/0041213 A1 | 2/2013 | Chechik | |
| 2013/0079588 A1 | 3/2013 | Crabtree et al. | |
| 2014/0155691 A1 | 6/2014 | Chechik | |
| 2014/0275745 A1 | 9/2014 | Intoccia, Jr. et al. | |

FOREIGN PATENT DOCUMENTS

| | | | |
|---|---|---|---|
| FR | 2041444 A5 * | 1/1971 | A61F 2/004 |
| FR | 2373272 A1 | 7/1978 | |
| FR | 2856582 A1 | 12/2004 | |
| FR | 2944430 A1 | 10/2010 | |
| GB | 2355937 A1 | 5/2001 | |
| WO | 2009055887 A2 | 5/2009 | |
| WO | 2013020555 A2 | 2/2013 | |

* cited by examiner

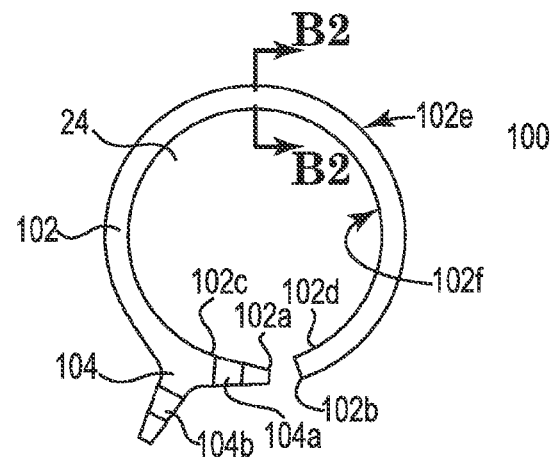
Fig. 2A
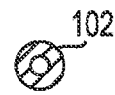
Fig. 2B
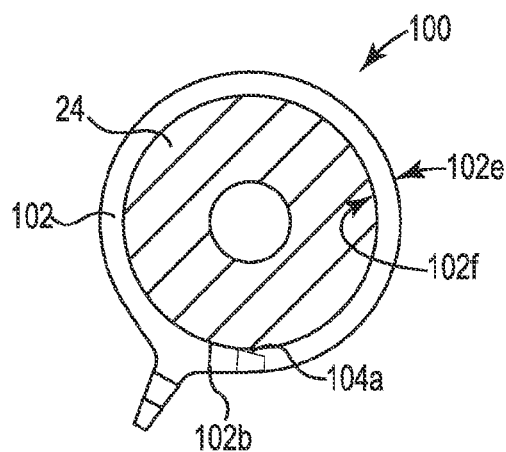 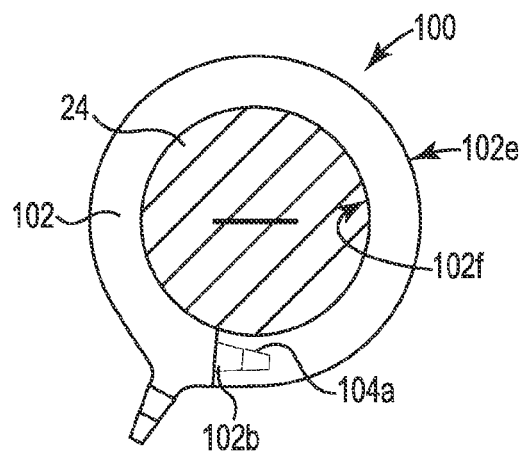
Fig. 2C                              Fig. 2D

CONNECTOR CUFF

BACKGROUND

Urinary incontinence affects many people and is a worldwide health issue. Published research indicates that urinary incontinence presents a substantial social and economic burden worldwide, affecting up to a mean of about 16% of the global population.

Urinary incontinence in women can be associated with a prolapse of one or more pelvic organs, which can arise from child birth or a weakness in the tissues/muscle of the pelvic floor. Urinary incontinence in men can arise after surgical treatment of the prostate gland, which treatment can include removal or weakening of the prostatic sphincter of the urinary urethra.

One treatment for urinary incontinence includes placing an artificial sphincter around a circumference of a portion of the urethra. The artificial sphincter operates to compress the urethra to selectively coapt or stop the flow of urine through the urethra, thus providing the user with a continent state. The artificial sphincter can be activated to an open position by the user, which opens the urethra and allows the user to selectively pass urine.

Surgeons and patients would welcome advances in the treatment of urinary incontinence.

SUMMARY

Some embodiments of the disclosure provide an artificial urinary sphincter (AUS) system that includes an elastic tube to be wrapped around a urethra and having at least one connector. The elastic tube has a first end to receive and dispatch fluid and a second end to be connected to the at least one connector. The elastic tube receives and dispatches the fluid to expand and contract the elastic tube and to coapt the urethra for continence and open the urethra for voiding.

Some embodiments of the disclosure provide an AUS system that includes an elastic tube and a connector. The elastic tube is configured to be wrapped around a urethra and has a first end and a second end. The connector is configured to receive fluid and has a first connector and a second connector. The first connector is to be connected to the first end and the second connector is to be connected to the second end, such that the elastic tube receives and dispatches the fluid to coapt the urethra for continence and open the urethra for voiding.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2A is a diagram illustrating one embodiment of a cuff that includes an elastic tube having a connector.

FIG. 2B is a cross-section of the elastic tube taken along the line B2-B2 in FIG. 2A.

FIG. 2C is a diagram illustrating the elastic tube situated around the urethra, where the elastic tube is deflated and the urethra is open for voiding.

FIG. 2D is a diagram illustrating the elastic tube situated around the urethra, where the elastic tube is inflated and the urethra is closed off to prevent incontinence.

DETAILED DESCRIPTION

Figure 1:
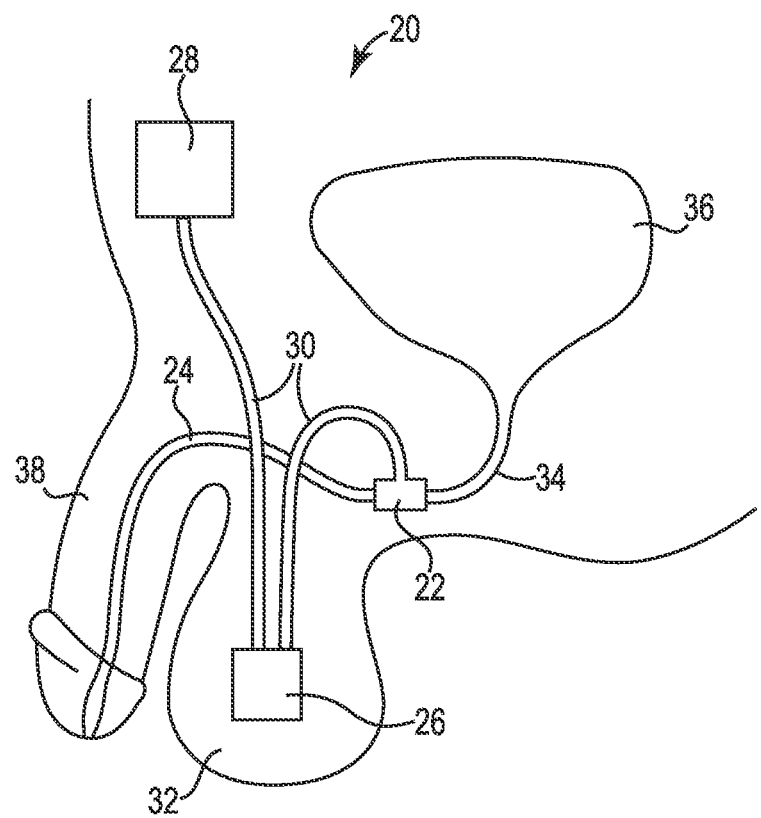
FIG. 1 is a perspective view of one embodiment of an AUS system illustrated as implanted in the environment of the male urogenital region.

In the following Detailed Description, reference is made to the accompanying drawings, which form a part hereof, and in which is shown by way of illustration embodiments. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the disclosure. The following detailed description, therefore, is not to be taken in a limiting sense.

The features of the various exemplary embodiments described in this disclosure may be combined with each other ("mixed and matched"), unless specifically noted otherwise.

Soft tissue includes dermal tissue, sub-dermal tissue, ligaments, tendons, or membranes but does not include bone.

End means endmost. A distal end is the furthest endmost location of a distal portion of a thing being described, whereas a proximal end is the nearest endmost location of a proximal portion of the thing being described. The portion next to or adjacent to an end is an end portion.

Artificial urinary sphincters have proved useful in the treatment of urinary incontinence. An AUS is implanted around the urethra and operable to selectively coapt the lumen of the urethra to allow the user to shift the artificial sphincter from an open state that allows urine to pass to a closed state that provides the user with continence.

One urinary control system that has found favor with the medical community includes three components cooperatively attached with tubing. The three components include an occlusive cuff, a control pump, and a pressure-regulating balloon reservoir. The cuff is implanted around the urethra, the control pump is implanted in the scrotum of a male user, and the pressure-regulating balloon reservoir is implanted in the prevesical space. The three components are filled with a liquid to provide a liquid-filled closed system that is maintained at an equilibrium pressure that closes the cuff around the urethra. When the user wishes to void, he squeezes and releases the pump several times to move fluid from the cuff into the pressure-regulating balloon reservoir. The cuff "deflates" and opens, which allows the urethra to open and pass urine. The pressure-regulating balloon reservoir, having been pressurized to a pressure above the equilibrium pressure by action of the pump, eventually automatically re-pressurizes the cuff to the equilibrium pressure over the course of several minutes to again inflate the cuff and coapt the urethra. The cuff is fabricated from sheets of film that are sealed to provide one or more inflatable cushions. The cuff is provided in a rectangular shape and intended to be placed around the urethra, with the ends of the rectangular cuff secured together. However, observers have noticed that the cuff of this system has a tendency to kink when it inflates, particularly at the junction of where the rectangular balloon cushions are formed into a circular cuff. The location of this kink can wear over time and create a leak in the cuff.

Embodiments described in this disclosure provide an AUS system that includes a cuff configured for placement around the urethra. The cuff includes an elastic tube to be wrapped around the urethra and a connector for connecting the elastic tube around the urethra and for connecting the elastic tube to a fluid control device. In some embodiments, the connector is built into and part of the elastic tube. In some embodiments, the connector is a separate device that is connected to multiple ends of the elastic tube.

The elastic tube can be a pre-shaped elastic tube that is formed to fit around the urethra. In some embodiments, the elastic tube is inflated to expand and coapt the urethra to maintain continence and deflated to contract and open the urethra for voiding. In some embodiments, the elastic tube is inflated to expand and open the urethra for voiding and deflated to contract and coapt the urethra to maintain continence or prevent incontinence.

Embodiments of the AUS system described in this disclosure further include a fluid reservoir that holds a fluid, such as a saline solution, and a control device that includes a pump and controls movement of the fluid between the fluid reservoir and the elastic tube.

The AUS systems described in this disclosure are suited for use in both female patients and male patients, where the cuff is placed around a portion of the urethra. Female patients can have the control device component implanted in one of the labia or an abdominal area. Male patients can have the control device component implanted in the scrotum.

FIG. 1 is a perspective view of one embodiment of an AUS system 20 illustrated as implanted in the environment of the male urogenital region. The AUS system 20 includes a cuff 22 situated around the urethra 24. The AUS system 20 also includes a control device 26 that is fluidically coupled to the cuff 22 and to a fluid reservoir 28 via tubing 30, such as kink-resistant tubing.

The cuff 22 includes an elastic tube that is wrapped around the urethra 24 and a connector that connects the elastic tube around the urethra 24 and to the control device 26. In some embodiments, the cuff 22 is inflated to expand the elastic tube and coapt or close off the urethra 24 to prevent incontinence and deflated to contract the elastic tube and open the urethra 24 for voiding. In some embodiments, the cuff 22 is inflated to expand the elastic tube and open the urethra 24 for voiding and deflated to contract the elastic tube and coapt or close off the urethra 24 to maintain continence.

The control device 26 and the fluid reservoir 28 are operable to inflate and deflate the cuff 22. The fluid reservoir 28 is sized to retain a volume of liquid that can be moved into the cuff 22 to expand the elastic tube.

In some embodiments, the fluid reservoir 28 provides a regulated fluid pressure and the control device 26 includes a control valve that, upon activation, allows the fluid to move from the fluid reservoir 28 into the cuff 22. This expands the cuff 22 to coapt or close off the urethra 24 to maintain continence. In some of these embodiments, the control device 26 includes a pump bulb that, upon squeezing, moves the fluid from the cuff 22 to the fluid reservoir 28 to deflate the cuff 22, where the bias of the elastic tube in the cuff 22 assists in deflating the cuff 22. The deflated cuff 22 allows the urethra 24 to open for voiding. In some embodiments, the fluid reservoir 28 that provides a regulated fluid pressure, automatically inflates the cuff 22 over time, such as 2 or 3 minutes or less, through a leaky valve arrangement in the control device 26 and the cuff 22, which expands the cuff 22 to coapt or close off the urethra 24 to prevent incontinence. In some embodiments, other suitable pumps are used, such as electromechanical pumps, electronic pumps, and button-style cavity pumps.

In some embodiments, the fluid reservoir 28 provides a regulated fluid pressure and the control device 26 includes a control valve that, upon activation, allows the fluid to move from the fluid reservoir 28 into the cuff 22. This expands the cuff 22 to allow the urethra 24 to open for voiding. In some of these embodiments, the control device 26 includes a pump bulb that, upon squeezing, moves the fluid from the cuff 22 to the fluid reservoir 28 to deflate the cuff 22, where the bias of the elastic tube in the cuff 22 assists in deflating the cuff 22. The deflated cuff 22 coapts or closes off the urethra 24 to maintain continence. In some embodiments, other suitable pumps are used, such as electromechanical pumps, electronic pumps, and button-style cavity pumps.

In some embodiments, the fluid reservoir 28 does not provide a regulated fluid pressure and the control device 26 includes a pump bulb that, upon squeezing, moves the fluid from the fluid reservoir 28 to the cuff 22. This expands the cuff 22 to coapt or close off the urethra 24. In some of these embodiments, the control device 26 includes a control valve that, upon activation, allows the fluid to move from the cuff 22 into the fluid reservoir 28, where the bias of the elastic tube in the cuff 22 assists in deflating the cuff 22. This deflates the cuff 22 to allow the urethra 24 to open for voiding. In some embodiments, other suitable pumps are used, such as electromechanical pumps, electronic pumps, and button-style cavity pumps.

In some embodiments, the fluid reservoir 28 does not provide a regulated fluid pressure and the control device 26 includes a pump bulb that, upon squeezing, moves the fluid from the fluid reservoir 28 to the cuff 22. This expands the cuff 22 to allow the urethra 24 to open for voiding. In some of these embodiments, the cuff 22 automatically deflates over time, such as 2 or 3 minutes or less, through a leaky valve arrangement in the control device 26 and the cuff 22, where the bias of the elastic tube in the cuff 22 assists in deflating the cuff 22. The deflated cuff 22 coapts or closes off the urethra 24 to prevent incontinence. In some embodiments, other suitable pumps are used, such as electromechanical pumps, electronic pumps, and button-style cavity pumps.

The control device 26 can be implanted within the scrotum 32, which provides access to the control device 26 by the user. Also, other locations for placement of the control device 26 are acceptable, for example as determined by the gender of the user.

The tubing 30 is provided in a kink resistant form and includes some style of connector that allows segments of the tubing 30 to be attached together after the various components, such as the control device 26 and the fluid reservoir 28, are primed with liquid. The tubing 30 is a thin-walled tube that is attachable between the control device 26 and the fluid reservoir 28, and between the control device 26 and the cuff 22. In one embodiment, the tubing 30 is separate from the control device 26 and separate from the fluid reservoir 28 and connects to these components through a locking mechanism, such as a quick connector or other suitable snap-fit connector.

The cuff 22 is implanted around the bulbous urethra or around the portion of the urethra 24 descending from the bladder neck 34. The cuff 22 is sized to allow placement as close to the bladder 36 as possible (desired by some surgeons), or positioned distal the bladder neck 34 as suitably determined by the attending surgeon. As illustrated in FIG. 1, the cuff 22 is implanted around the urethra 24 at a location where the urethra 24 transitions from a vertical orientation communicating with the bladder 36 to a horizontal orientation extending to the penis 38, which desirably corresponds to the area of the urogenital region associated with an increased level of muscle mass.

FIG. 2A is a diagram illustrating one embodiment of a cuff 100 that includes an elastic tube 102 having a connector 104. In some embodiments, the cuff 100 is similar to the cuff 22 (shown in FIG. 1).

The elastic tube 102 has a first end 102a and a second end 102b, where the connector 104 is formed into the elastic tube 102 at a first end portion 102c of the elastic tube 102 that is adjacent the first end 102a. The connector 104 includes a first connector 104a and a second connector 104b. The first connector 104a is suitable for attachment to the second end 102b of the elastic tube 102, such that the second end 102b and a second end portion 102d of the elastic tube 102 that is adjacent the second end 102b engage the first connector 104a to provide a snug, fluid tight fit. The second connector 104b is suitable for attachment to tubing, such as tubing 30 (shown in FIG. 1).

The elastic tube 102 and connector 104 fit around the urethra 24. The elastic tube 102 and the connector 104 form an annular ring around the urethra 24. The elastic tube 102 has an exterior surface 102e that is the outermost portion of the elastic tube 102 and an inner surface 102f that is provided to contact the urethra 24. The exterior surface 102e is opposite of or 180 degrees displaced from the inner surface 102f of the tube 102.

The elastic tube 102 is made out of an elastic material, such that the elastic tube 102 expands upon being filled with fluid from a fluid reservoir, such as the fluid reservoir 28. In some embodiments, the elastic tube 102 includes a urethane elastomer. In some embodiments, the elastic tube 102 includes a urethane elastomer having a wall thickness of between 0.25 and 2 millimeters (mm), such as a wall thickness of 0.75 mm. In some embodiments, the elastic tube 102 includes silicone. In some embodiments, the elastic tube 102 includes silicone having a wall thickness of between 1 and 2 mm.

FIG. 2B is a cross-section of the elastic tube 102 taken along the line B2-B2 in FIG. 2A. The elastic tube 102 has a circular cross-section from the connector 104 to the second end 102b.

In other embodiments, the elastic tube 102 has a circular cross-section adjacent the connector 104 and adjacent the second end 102b, but a flattened or oblong shaped cross-section at a back portion of the elastic tube 102, which is opposite the connector 104, such as at the line B2-B2 in FIG. 2A. In some embodiments, the elastic tube 102 has a flattened out or oblong shaped cross-section from the connector 104 to the second end 102b. In some embodiments, the elastic tube 102 is flattened on the exterior surface 102e, at least opposite the connector 104, such as at the line B2-B2 in FIG. 2A, to provide a backboard that is placed against tough, supporting fascia tissue superior to the urethra 24 when the patient is standing or distal to the urethra 24 when the patient is lying on their back. In all of these embodiments, the flattened out or oblong shaped cross-section of the elastic tube 102 fits behind the urethra 24 with the elastic tube 102 situated around the urethra 24.

The elastic tube 102 and connector 104 are sized to fit around the urethra 24. To put the cuff 100 around the urethra 24, the second end 102b of the elastic tube 102 is slid behind the urethra 24 to emerge from the other side of the urethra 24. The second end 102b is then connected to the first connector 104a to connect the elastic tube 102 around the urethra 24. In some embodiments, the elastic tube 102 is pre-shaped or pre-formed to fit around the urethra, such that the elastic tube 102 does not kink or wrinkle as it is wrapped around the urethra 24. In some embodiments, the elastic tube 102 is pre-shaped or pre-formed into a circular shape to fit around the urethra, such that the elastic tube 102 does not kink or wrinkle as it is wrapped around the urethra 24. In some embodiments, the elastic tube 102 is pre-shaped or pre-formed into an oblong or oval shape to fit around the urethra, such that the elastic tube 102 does not kink or wrinkle as it is wrapped around the urethra 24.

FIGS. 2C and 2D are diagrams illustrating one embodiment of the cuff 100 that is deflated to contract the elastic tube 102 to open the urethra 24 for voiding, and inflated to expand the elastic tube 102 to coapt or close off the urethra 24 to prevent incontinence. FIG. 2C is a diagram illustrating the elastic tube 102 situated around the urethra 24, where the elastic tube 102 is deflated and the urethra 24 is open for voiding. FIG. 2D is a diagram illustrating the elastic tube 102 situated around the urethra 24, where the elastic tube 102 is inflated and the urethra 24 is closed off to prevent incontinence. The second end 102b of the elastic tube 102 is connected to the first connector 104a, and the second connector 104b is connected to tubing (not shown), such as tubing 30, for receiving and dispatching the fluid.

In operation, as described in reference to FIG. 1, a control device such as control device 26 and a fluid reservoir such as fluid reservoir 28 cooperate to move fluid from the fluid reservoir to the elastic tube 102 of the cuff 100. This expands the elastic tube 102 and pinches off or closes the urethra 24 (as shown in FIG. 2D). After some time, the fluid is removed from the elastic tube 102, which relaxes or contracts the elastic tube 102 from around the urethra 24 to allow the urethra 24 to open for voiding (as shown in FIG. 2C). The control device and the fluid reservoir further cooperate to move fluid from the fluid reservoir to the elastic tube 102 to expand the elastic tube 102 and close the urethra 24 to prevent incontinence.

Figure 3A:
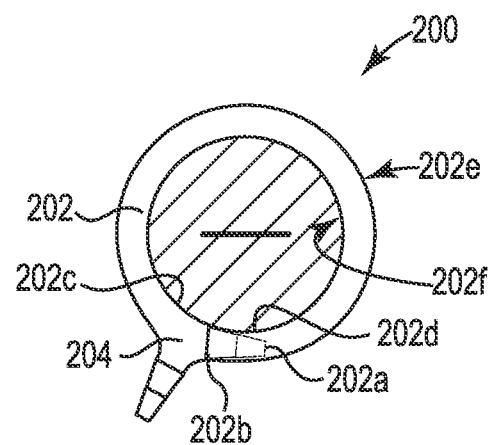
FIG. 3A is a diagram illustrating an elastic tube situated around the urethra, where the elastic tube is deflated and contracted to pinch off or close the urethra to prevent incontinence.
Figure 3B:
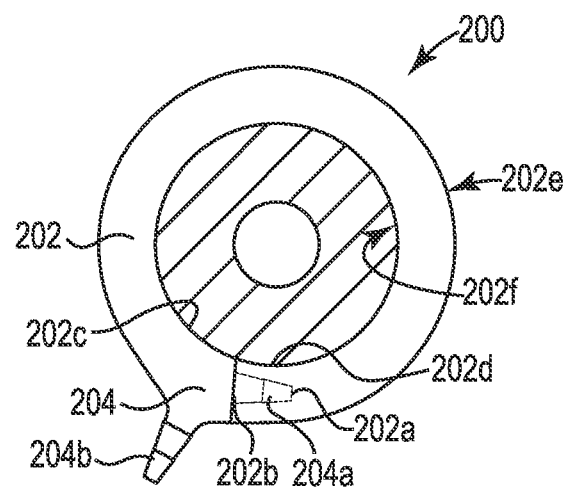
FIG. 3B is a diagram illustrating the elastic tube situated around the urethra, where the elastic tube is inflated and expanded to allow the urethra to open for voiding.

FIGS. 3A and 3B are diagrams illustrating one embodiment of a cuff 200 that is similar to the cuff 100, except the cuff 200 includes an elastic tube 202 having a connector 204, which is deflated to contract the elastic tube 202 to close off the urethra 24 to prevent incontinence, and inflated to expand the elastic tube 202 to allow the urethra 24 to open for voiding. In some embodiments, the cuff 100 is similar to the cuff 22 (shown in FIG. 1).

The elastic tube 202 has a first end 202a and a second end 202b, where the connector 204 is formed into the elastic tube 202 at a first end portion 202c of the elastic tube 202 that is adjacent the first end 202a. The connector 204 includes a first connector 204a and a second connector 204b. The first connector 204a is suitable for attachment to the second end 202b of the elastic tube 202, such that the second end 202b and a second end portion 202d of the elastic tube 202 that is adjacent the second end 202b engage the first connector 204a to provide a snug, fluid tight fit. The second connector 204b is suitable for attachment to tubing, such as tubing 30 (shown in FIG. 1).

The elastic tube 202 and connector 204 fit around the urethra 24. The elastic tube 202 and the connector 204 form an annular ring around the urethra 24. The elastic tube 202 has an exterior surface 202e that is the outermost portion of the elastic tube 202 and an inner surface 202f that is provided to contact the urethra 24. The exterior surface 202e is opposite of or 180 degrees displaced from the inner surface 202f.

The elastic tube 202 is made out of an elastic material, such that the elastic tube 202 expands upon being filled with fluid from a fluid reservoir, such as the fluid reservoir 28. The elastic tube 202 has a circular cross-section from the connector 204 to the second end 202b. In some embodiments, the elastic tube 202 includes a urethane elastomer. In some embodiments, the elastic tube 202 includes a urethane elastomer having a wall thickness of between 0.25 and 2 millimeters (mm), such as a wall thickness of 0.75 mm. In some embodiments, the elastic tube 202 includes silicone. In some embodiments, the elastic tube 202 includes silicone having a wall thickness of between 1 and 2 mm.

Figure 4A:
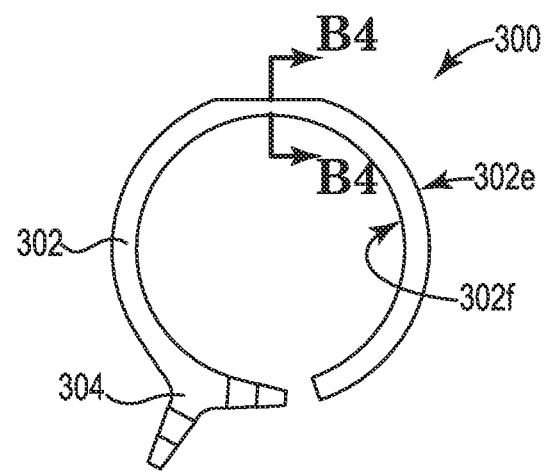
FIG. 4A is a top-view diagram of a cuff that includes an elastic tube having a connector, where the elastic tube has a flattened out cross-section at the back portion of the elastic tube.

In other embodiments, the elastic tube 202 has a circular cross-section adjacent the connector 204 and adjacent the second end 202b, but a flattened or oblong shaped cross-section at a back portion of the elastic tube 202, which is opposite the connector 204, such as illustrated at the line B4-B4 in FIG. 4A in reference to the connector 304. In some embodiments, the elastic tube 202 has a flattened out or oblong shaped cross-section from the connector 204 to the second end 202b. In some embodiments, the elastic tube 202 is flattened on the exterior surface 202e, at least opposite the connector 204, to provide a backboard that is placed against tough, supporting fascia tissue superior to the urethra 24 when the patient is standing or distal to the urethra 24 when the patient is lying on their back. In all of these embodiments, the flattened out or oblong shaped cross-section of the elastic tube 202 fits behind the urethra 24 with the elastic tube 202 situated around the urethra 24.

The elastic tube 202 and connector 204 are sized to fit around the urethra 24. To put the cuff 200 around the urethra 24, the second end 202b of the elastic tube 202 is slid behind the urethra 24 to emerge from the other side of the urethra 24. The second end 202b is then connected to the first connector 204a to connect the elastic tube 202 around the urethra 24. In some embodiments, the elastic tube 202 is pre-shaped or pre-formed to fit around the urethra, such that the elastic tube 202 does not kink or wrinkle as it is wrapped around the urethra 24. In some embodiments, the elastic tube 202 is pre-shaped or pre-formed into a circular shape to fit around the urethra, such that the elastic tube 202 does not kink or wrinkle as it is wrapped around the urethra 24. In some embodiments, the elastic tube 202 is pre-shaped or pre-formed into an oblong or oval shape to fit around the urethra, such that the elastic tube 202 does not kink or wrinkle as it is wrapped around the urethra 24.

FIG. 3A is a diagram illustrating the elastic tube 202 situated around the urethra 24, where the elastic tube 202 is deflated and contracted to pinch off or close the urethra 24 to prevent incontinence. FIG. 3B is a diagram illustrating the elastic tube 202 situated around the urethra 24, where the elastic tube 202 is inflated and expanded to allow the urethra 24 to open for voiding. The second end 202b of the elastic tube 202 is connected to the first connector 204a, and the second connector 204b is connected to tubing (not shown), such as tubing 30, for receiving and dispatching the fluid.

In operation, as described in reference to FIG. 1, a control device such as control device 26 and a fluid reservoir such as fluid reservoir 28 cooperate to move fluid from the fluid reservoir to the elastic tube 202 of the cuff 200. This expands the elastic tube 202 from around the urethra 24 and allows the urethra 24 to open for voiding (as shown in FIG. 3B). After some time, the fluid is removed from the elastic tube 202, which contracts the elastic tube 202 to tighten around the urethra 24 and to close off the urethra 24 to prevent incontinence (as shown in FIG. 3A).

Figure 4B:
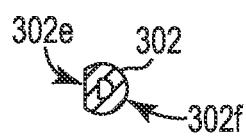
FIG. 4B is a side-view cross-section diagram of the elastic tube taken along the line B4-B4 in FIG. 4A.

FIGS. 4A and 4B are diagrams illustrating one embodiment of a cuff 300 that has a flattened out cross-section at the back portion of the elastic tube 302, opposite the connector 304. In some embodiments, the cuff 300 is similar to the cuff 22 (shown in FIG. 1).

FIG. 4A is a top-view diagram of the cuff 300 that includes an elastic tube 302 having a connector 304, as described above in reference to either the cuff 100 or the cuff 200, with the exception that the elastic tube 302 of the cuff 300 has a flattened out cross-section at the back portion of the elastic tube 302, such as at the line B4-B4 in FIG. 4A.

The elastic tube 302 and connector 304 fit around the urethra 24. The elastic tube 302 and the connector 304 form an annular ring around the urethra 24. The elastic tube 302 has an exterior surface 302e that is the outermost portion of the elastic tube 302 and an inner surface 302f that is provided to contact the urethra 24. The exterior surface 302e is opposite of or 180 degrees displaced from the inner surface 302f.

In some embodiments, the elastic tube 302 has a circular cross-section adjacent the connector 304 and adjacent the second end 302b, but a flattened out cross-section at the back portion of the elastic tube 302, which is opposite the connector 304, such as at the line B4-B4 in FIG. 4A. In some embodiments, the elastic tube 302 has a flattened out cross-section from the connector 304 to the second end 302b. In some embodiments, the elastic tube 302 is flattened on the exterior surface 302e, at least opposite the connector 304, such as at the line B4-B4 in FIG. 4A, to provide a backboard that is placed against tough, supporting fascia tissue superior to the urethra 24 when the patient is standing or distal to the urethra 24 when the patient is lying on their back. In any of these embodiments, the flattened out cross-section of the elastic tube 302 fits comfortably behind the urethra 24 with the elastic tube 302 situated around the urethra 24.

FIG. 4B is a side-view cross-section diagram of the elastic tube 302 taken along the line B4-B4 in FIG. 4A, which illustrates the elastic tube 302 as being flattened out on the exterior surface 302e of the elastic tube 302, opposite the inner surface 302f.

Figure 5A:
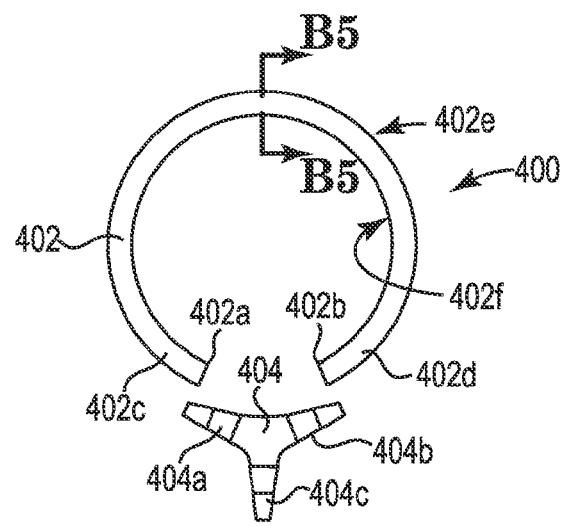
FIG. 5A is a diagram illustrating one embodiment of a cuff that includes an elastic tube and a connector that is not part of the elastic tube.

FIG. 5A is a diagram illustrating one embodiment of a cuff 400 that includes an elastic tube 402 and a connector 404 that is not part of the elastic tube 402. In some embodiments, the cuff 400 is similar to the cuff 22 (shown in FIG. 1).

The elastic tube 402 has a first end 402a and a second end 402b, and the connector 404 has a first connector 404a, a second connector 404b, and a third connector 404c. The first connector 404a is suitable for attachment to the first end 402a, such that the first end 402a and a first end portion 402c of the elastic tube 402 that is adjacent the first end 402a engage the first connector 404a to provide a snug, fluid tight fit. The second connector 404b is suitable for attachment to the second end 402b, such that the second end 402b and a second end portion 402d of the elastic tube 402 that is adjacent the second end 402b engage the second connector 404b to provide a snug, fluid tight fit. The third connector 404c is suitable for attachment to tubing, such as tubing 30 (shown in FIG. 1).

The elastic tube 402 and connector 404 fit around the urethra 24. The elastic tube 402 and the connector 404 form an annular ring around the urethra 24. The elastic tube 402 has an exterior surface 402e that is the outermost portion of the elastic tube 402 and an inner surface 402f that is provided to contact the urethra 24. The exterior surface 402e is opposite of or 180 degrees displaced from the inner surface 402f.

The elastic tube 402 is made out of an elastic material, such that the elastic tube 402 expands upon being filled with fluid from a fluid reservoir, such as the fluid reservoir 28. In some embodiments, the elastic tube 402 includes a urethane elastomer. In some embodiments, the elastic tube 402 includes a urethane elastomer having a wall thickness of between 0.25 and 2 millimeters (mm), such as a wall thickness of 0.75 mm. In some embodiments, the elastic tube 402 includes silicone. In some embodiments, the elastic tube 402 includes silicone having a wall thickness of between 1 and 2 mm.

Figure 5B:
FIG. 5B is a cross-section of the elastic tube taken along the line B5-B5 in FIG. 5A.

FIG. 5B is a cross-section of the elastic tube 402 taken along the line B5-B5 in FIG. 5A. The elastic tube 402 has a circular cross-section from the first end 402a to the second end 402b.

In other embodiments, the elastic tube 402 has a circular cross-section adjacent the first end 402a and adjacent the second end 402b, but a flattened or oblong shaped cross-section at a back portion of the elastic tube 402, which is opposite the connector 404, such as at the line B5-B5 in FIG. 5A. In some embodiments, the elastic tube 402 has a flattened out or oblong shaped cross-section from the first end 404a to the second end 402b. In some embodiments, the elastic tube 402 is flattened on the exterior surface 402e, at least opposite the connector 404, such as at the line B5-B5 in FIG. 5A, to provide a backboard that is placed against tough, supporting fascia tissue superior to the urethra 24 when the patient is standing or distal to the urethra 24 when the patient is lying on their back. In any of these embodiments, the flattened out or oblong shaped cross-section of the elastic tube 402 fits behind the urethra 24 with the elastic tube 402 situated around the urethra 24.

The elastic tube 402 and the connector 404 are sized to fit around the urethra 24. To put the cuff 400 around the urethra 24, one of the first and second ends 402a and 402b of the elastic tube 402 is slid behind the urethra 24 to emerge from the other side of the urethra 24. The first and second ends 402a and 402b are then connected to the first and second connectors 404a and 404b, respectively. In some embodiments, one of the first and second ends 402a and 402b is connected to its corresponding first or second connector 404a or 404b and the other one of the first and second ends 402a and 402b is slid behind the urethra 24 to emerge from the other side of the urethra 24. The end slid behind the urethra 24 is then connected to its corresponding one of the first and second connectors 404a and 404b to connect the elastic tube 402 around the urethra 24.

In some embodiments, the elastic tube 402 is pre-shaped or pre-formed to fit around the urethra 24, such that the elastic tube 402 does not kink or wrinkle as it is wrapped around the urethra 24. In some embodiments, the elastic tube 402 is pre-shaped or pre-formed into a circular shape to fit around the urethra 24, such that the elastic tube 402 does not kink or wrinkle as it is wrapped around the urethra 24. In some embodiments, the elastic tube 402 is pre-shaped or pre-formed into an oblong or oval shape to fit around the urethra 24, such that the elastic tube 402 does not kink or wrinkle as it is wrapped around the urethra 24.

Figures 5C, 5D:
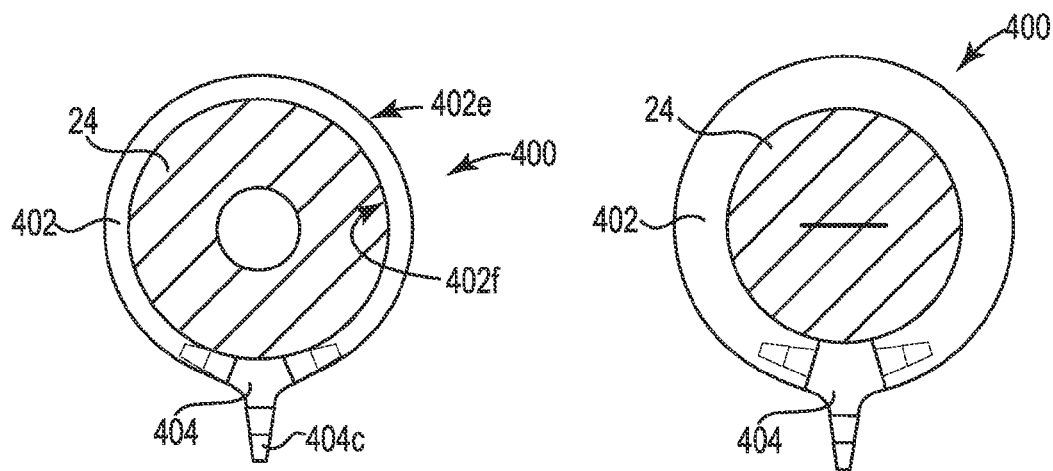
FIG. 5C is a diagram illustrating the elastic tube and the connector situated around the urethra, where the elastic tube is deflated and the urethra is open for voiding.
FIG. 5D is a diagram illustrating the elastic tube and the connector situated around the urethra, where the elastic tube is inflated and the urethra is closed off to prevent incontinence.

FIGS. 5C and 5D are diagrams illustrating one embodiment of the cuff 400 that is deflated to contract the elastic tube 402 to open the urethra 24 for voiding, and inflated to expand the elastic tube 402 to coapt or close off the urethra 24 to prevent incontinence. FIG. 5C is a diagram illustrating the elastic tube 402 and the connector 404 situated around the urethra 24, where the elastic tube 402 is deflated and the urethra 24 is open for voiding. FIG. 5D is a diagram illustrating the elastic tube 402 and the connector 404 situated around the urethra 24, where the elastic tube 402 is inflated and the urethra 24 is closed off to prevent incontinence. The first and second ends 402a and 402b of the elastic tube 402 are connected to the first and second connectors 404a and 404b, respectively, and the third connector 404c is connected to tubing (not shown), such as tubing 30, for receiving and dispatching the fluid.

In operation, as described in reference to FIG. 1, a control device such as control device 26 and a fluid reservoir such as fluid reservoir 28 cooperate to move fluid from the fluid reservoir to the elastic tube 402 of the cuff 400. This expands the elastic tube 402 and pinches off or closes the urethra 24 (as shown in FIG. 5D). After some time, the fluid is removed from the elastic tube 402, which relaxes or contracts the elastic tube 402 from around the urethra 24 to allow the urethra 24 to open for voiding (as shown in FIG. 5C). The control device and the fluid reservoir further cooperate to move fluid from the fluid reservoir to the elastic tube 402 to expand the elastic tube 402 and close the urethra 24 to prevent incontinence.

Figure 6A:
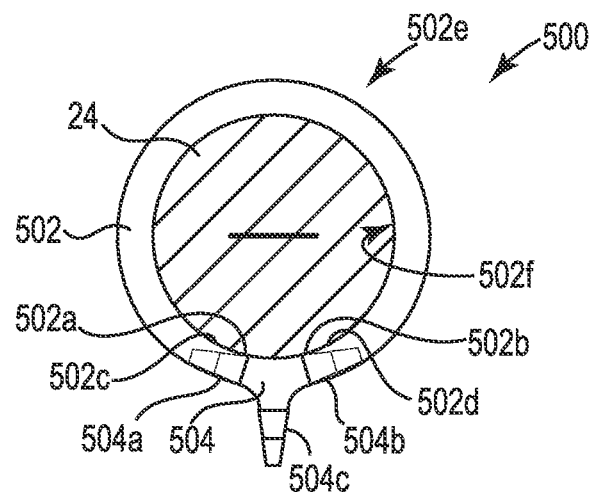
FIG. 6A is a diagram illustrating an elastic tube situated around the urethra, where the elastic tube is deflated and contracted to pinch off or close the urethra to prevent incontinence.
Figure 6B:
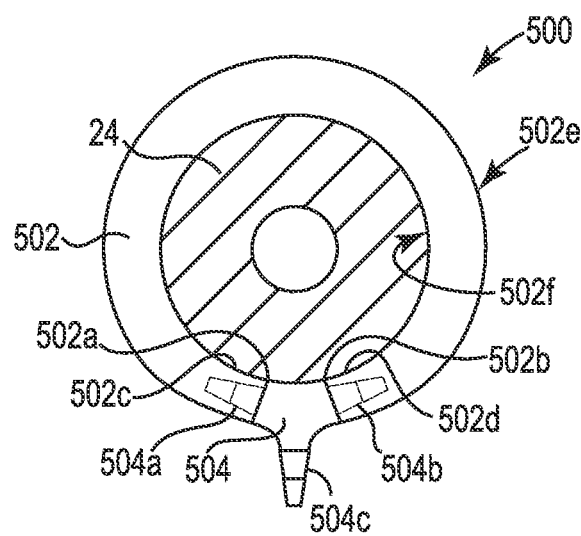
FIG. 6B is a diagram illustrating the elastic tube situated around the urethra, where the elastic tube is inflated and expanded to allow the urethra to open for voiding.

FIGS. 6A and 6B are diagrams illustrating one embodiment of a cuff 500 that is similar to the cuff 400, except the cuff 500 includes an elastic tube 502 and a connector 504, which is deflated to contract the elastic tube 502 to close off the urethra 24 to prevent incontinence, and inflated to expand the elastic tube 502 to allow the urethra 24 to open for voiding. In some embodiments, the cuff 500 is similar to the cuff 22 (shown in FIG. 1).

The elastic tube 502 has a first end 502a and a second end 502b, and the connector 504 has a first connector 504a, a second connector 504b, and a third connector 504c. The first connector 504a is suitable for attachment to the first end 502a, such that the first end 502a and a first end portion 502c of the elastic tube 502 that is adjacent the first end 502a engage the first connector 504a to provide a snug, fluid tight fit. The second connector 504b is suitable for attachment to the second end 502b, such that the second end 502b and a second end portion 502d of the elastic tube 502 that is adjacent the second end 502b engage the second connector 504b to provide a snug, fluid tight fit. The third connector 504c is suitable for attachment to tubing, such as tubing 30 (shown in FIG. 1).

The elastic tube 502 and connector 504 fit around the urethra 24. The elastic tube 502 and the connector 504 form an annular ring around the urethra 24. The elastic tube 502 has an exterior surface 502e that is the outermost portion of the elastic tube 502 and an inner surface 502f that is provided to contact the urethra 24. The exterior surface 502e is opposite of or 180 degrees displaced from the inner surface 502f.

The elastic tube 502 is made out of an elastic material, such that the elastic tube 502 expands upon being filled with fluid from a fluid reservoir, such as the fluid reservoir 28. The elastic tube 502 has a circular cross-section from the first end 502a to the second end 502b. In some embodiments, the elastic tube 502 includes a urethane elastomer. In some embodiments, the elastic tube 502 includes a urethane elastomer having a wall thickness of between 0.25 and 2 millimeters (mm), such as a wall thickness of 0.75 mm. In some embodiments, the elastic tube 502 includes silicone. In some embodiments, the elastic tube 502 includes silicone having a wall thickness of between 1 and 2 mm.

In other embodiments, the elastic tube 502 has a circular cross-section adjacent the first end 502a and adjacent the second end 502b, but a flattened or oblong shaped cross-section at a back portion of the elastic tube 502, which is opposite the connector 504, such as at the line B6-B6 in FIG. 6A. In some embodiments, the elastic tube 502 has a flattened out or oblong shaped cross-section from the first end 502a to the second end 502b. In some embodiments, the elastic tube 502 is flattened on the exterior surface 502e, at least opposite the connector 504, such as at the line B5-B5 in FIG. 5A, to provide a backboard that is placed against tough, supporting fascia tissue superior to the urethra 24 when the patient is standing or distal to the urethra 24 when the patient is lying on their back. In any of these embodiments, the flattened out or oblong shaped cross-section of the elastic tube 502 fits comfortably behind the urethra 24 with the elastic tube 502 situated around the urethra 24.

The elastic tube 502 and the connector 504 are sized to fit around the urethra 24. To put the cuff 500 around the urethra 24, one of the first and second ends 502a and 502b of the elastic tube 502 is slid behind the urethra 24 to emerge from the other side of the urethra 24. The first and second ends 502a and 502b are then connected to the first and second connectors 504a and 504b, respectively. In some embodiments, one of the first and second ends 502a and 502b is connected to its corresponding first or second connector 504a or 504b and the other one of the first and second ends 502a and 502b is slid behind the urethra 24 to emerge from the other side of the urethra 24. The end slid behind the urethra 24 is then connected to its corresponding one of the first and second connectors 504a and 504b to connect the elastic tube 502 around the urethra 24.

In some embodiments, the elastic tube 502 is pre-shaped or pre-formed to fit around the urethra, such that the elastic tube 502 does not kink or wrinkle as it is wrapped around the urethra 24. In some embodiments, the elastic tube 502 is pre-shaped or pre-formed into a circular shape to fit around the urethra 24, such that the elastic tube 502 does not kink or wrinkle as it is wrapped around the urethra 24. In some embodiments, the elastic tube 502 is pre-shaped or pre-formed into an oblong or oval shape to fit around the urethra 24, such that the elastic tube 502 does not kink or wrinkle as it is wrapped around the urethra 24.

FIG. 6A is a diagram illustrating the elastic tube 502 situated around the urethra 24, where the elastic tube 502 is deflated and contracted to pinch off or close the urethra 24 to prevent incontinence. FIG. 6B is a diagram illustrating the elastic tube 502 situated around the urethra 24, where the elastic tube 502 is inflated and expanded to allow the urethra 24 to open for voiding. The first end 502a is connected to the first connector 504a, the second end 502b is connected to the second connector 504b, and the third connector 504c is connected to tubing (not shown), such as tubing 30, for receiving and dispatching the fluid.

In operation, as described in reference to FIG. 1, a control device such as control device 26 and a fluid reservoir such as fluid reservoir 28 cooperate to move fluid from the fluid reservoir to the elastic tube 502 of the cuff 500. This expands the elastic tube 502 from around the urethra 24 and allows the urethra 24 to open for voiding (as shown in FIG. 6B). After some time, the fluid is removed from the elastic tube 502, which contracts the elastic tube 502 to tighten around the urethra 24 and to close off the urethra 24 to prevent incontinence (as shown in FIG. 6A).

Figure 7A:
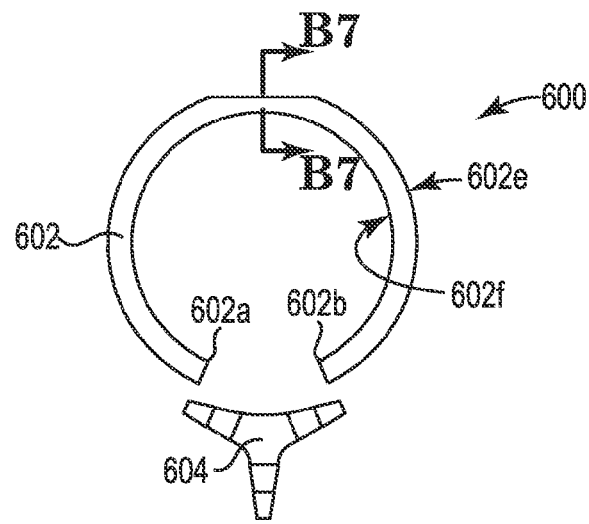
FIG. 7A is a top-view diagram of a cuff that includes an elastic tube and a connector, where the elastic tube of the cuff has a flattened out or oblong shaped cross-section at the back of the elastic tube.
Figure 7B:
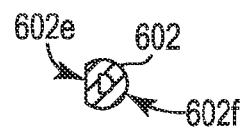
FIG. 7B is a side-view cross-section diagram of the elastic tube taken along the line B7-B7 in FIG. 7A.

FIGS. 7A and 7B are diagrams illustrating one embodiment of a cuff 600 that has a flattened out cross-section at the back portion of the elastic tube 602, opposite the connector 604. In some embodiments, the cuff 600 is similar to the cuff 22 (shown in FIG. 1).

FIG. 7A is a top-view diagram of the cuff 600 that includes an elastic tube 602 and a connector 604, as described above in reference to either the cuff 400 or the cuff 500, with the exception that the elastic tube 602 of the cuff 600 has a flattened out cross-section at the back portion of the elastic tube 602, such as at the line B7-B7 in FIG. 7A.

The elastic tube 602 and connector 604 fit around the urethra 24. The elastic tube 602 and the connector 604 form an annular ring around the urethra 24. The elastic tube 602 has an exterior surface 602e that is the outermost portion of the elastic tube 602 and an inner surface 602f that is provided to contact the urethra 24. The exterior surface 602e is opposite of or 180 degrees displaced from the inner surface 602f.

In some embodiments, the elastic tube 602 has a circular cross-section adjacent the first end 602a and the second end 602b, but a flattened out cross-section at the back portion of the elastic tube 602, which is opposite the connector 604, such as at the line B7-B7 in FIG. 7A. In some embodiments, the elastic tube 602 has a flattened out cross-section from the first end 602a to the second end 602b. In some embodiments, the elastic tube 602 is flattened on the exterior surface 602e, at least opposite the connector 604, such as at the line B7-B7 in FIG. 7A, to provide a backboard that is placed against tough, supporting fascia tissue superior to the urethra 24 when the patient is standing or distal to the urethra 24 when the patient is lying on their back. In any of these embodiments, the flattened out cross-section of the elastic tube 602 fits comfortably behind the urethra 24 with the elastic tube 602 situated around the urethra 24.

FIG. 7B is a side-view cross-section diagram of the elastic tube 602 taken along the line B7-B7 in FIG. 7A, which illustrates the elastic tube 602 as being flattened out on the exterior surface 602e of the elastic tube 602, opposite the inner surface 602f.

Figure 8:
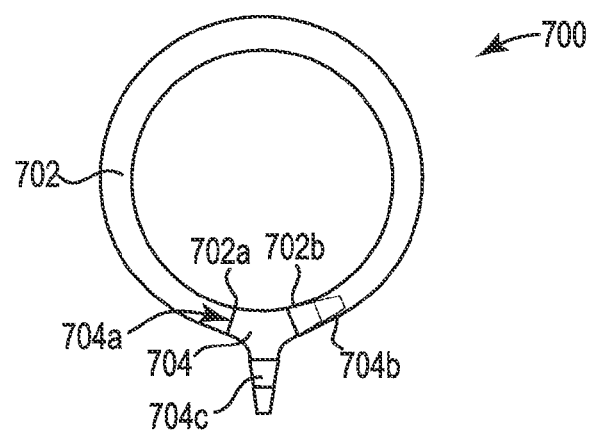
FIG. 8 is a diagram of one embodiment of a cuff, where one of the first and second ends of the elastic tube is over molded onto the corresponding one of the first and second connectors of the connector.

FIG. 8 is a diagram of one embodiment of a cuff 700, which is similar to at least one of the cuffs 400, 500, and 600, with the exception that one of the first and second ends 702a and 702b of the elastic tube 702 is over molded onto the corresponding one of the first and second connectors 704a and 704b of the connector 704. As illustrated, the first end 702a is over molded onto the first connector 704a.

Figure 9:
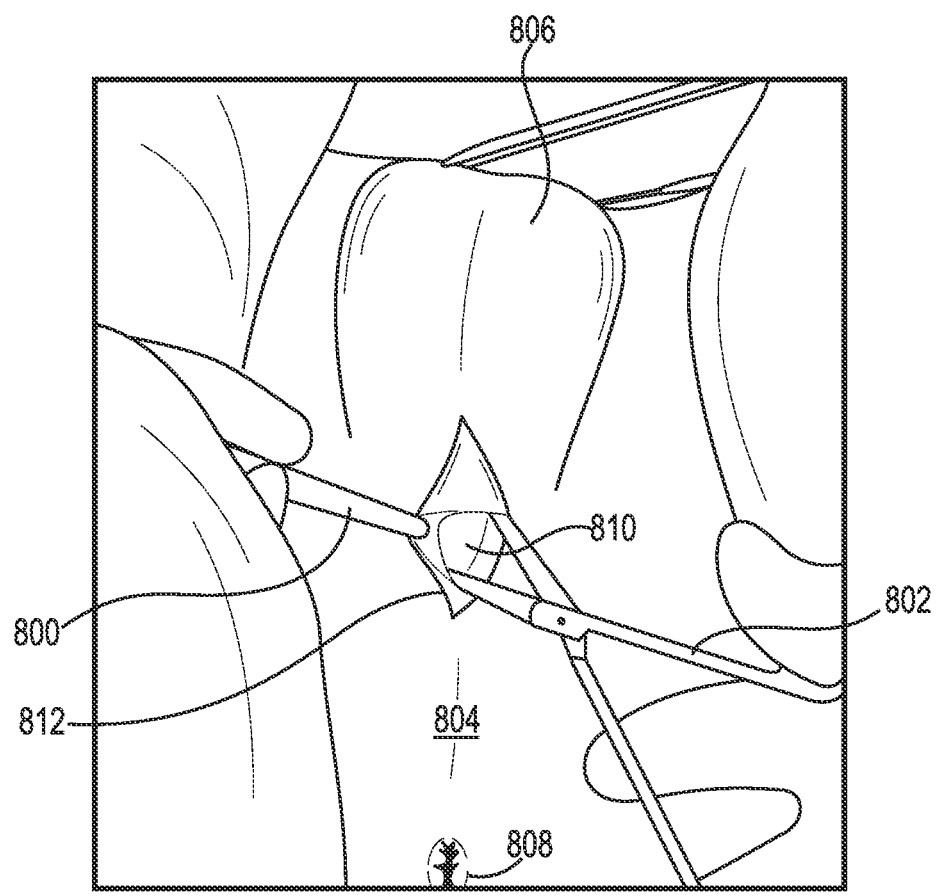
FIG. 9 is a schematic view of a scalpel and a dissection tool employed to dissect tissue through the perineum to expose the bulbar urethra.

FIG. 9 is a schematic view of a scalpel 800 and a dissection tool 802 employed to dissect tissue through the perineum 804, which is situated between the scrotum 806 and the anus 808, to expose the bulbar urethra 810. An incision 812 is made through the perineum 804 to dissect the tissue.

Figure 10:
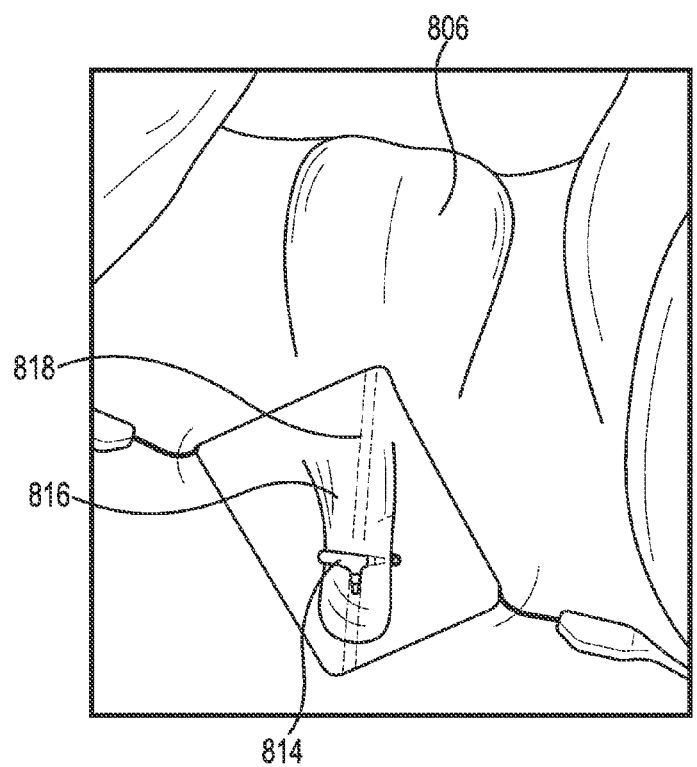
FIG. 10 is a schematic view of a cuff situated around the urethral bulb.

FIG. 10 is a schematic view of a cuff 814, such as one of the cuffs 22, 100, 200, 300, 400, 500, 600, and 700, situated around the urethral bulb 816. A urinary catheter 818 has been placed inside the bladder through the urethra to drain urine from the bladder, and the surgeon has dissected tissue away from and around the urethral bulb 816 for the suitable placement of the cuff 814.

Figure 11:
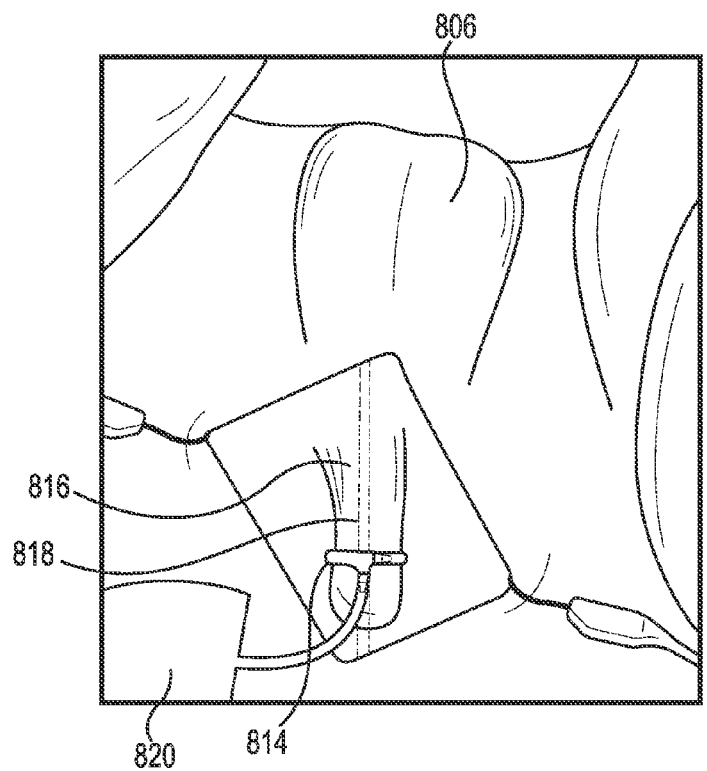
FIG. 11 is a schematic view of the cuff in place around the urethral bulb of the patient and connected to an AUS system.

FIG. 11 is a schematic view of the cuff 814 in place around the urethral bulb 816 of the patient and connected to an AUS system 820, similar to the AUS system 20 (shown in FIG. 1).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. An artificial urinary sphincter system, comprising:
an elastic tube to be wrapped around a urethra and having at least one connector, wherein the elastic tube has a first end that provides a first opening to receive and dispatch fluid, a second end that provides a second opening, and tubing between the first end and the second end, where the first end of the elastic tube is insertable into the second opening of the second end of the elastic tube to provide an annular elastic tube with an internal flow path that is continuous and annular around the annular elastic tube, such that the fluid can flow all the way around the annular elastic tube including from the second end into the first opening without flowing through the tubing between the first end and the second end;
wherein the annular elastic tube receives and dispatches the fluid to expand and contract the annular elastic tube and to coapt the urethra for continence and open the urethra for voiding;
wherein the at least one connector includes a first connector having an end that forms the first end of the elastic tube and a second connector having an end that is attachable to a separate section of tubing and adapted to communicate with a reservoir.

2. The system of claim 1, wherein an exterior surface of the elastic tube opposite of the at least one connector is flat to provide a backboard for placement against supporting fascia tissue superior to the urethra.

3. The system of claim 1, wherein the elastic tube is pre-shaped into one of a circular shape and an oval shape for wrapping around the urethra.

4. The system of claim 1, wherein the elastic tube is molded into the at least one connector and the first end is molded to receive a separate section of tubing.

5. The system of claim 1, wherein the elastic tube is fluidically connected to a control device that regulates flow of the fluid to and from the elastic tube.

6. The system of claim 5, comprising a reservoir to hold the fluid, wherein the control device includes a pump that transfers the fluid to one of the elastic tube to expand the elastic tube and the reservoir to deflate the elastic tube.

7. The system of claim 5, comprising a reservoir to hold the fluid, wherein the control device regulates the flow of the fluid between the reservoir and the elastic tube.

8. The system of claim 7, wherein the reservoir maintains an elevated fluid pressure, and the control device regulates the flow of the fluid from the reservoir to the elastic tube to inflate the elastic tube.

9. An artificial urinary sphincter system, comprising:
an elastic tube to be wrapped around a urethra, the elastic tube having an open first end and an open second end; and
a connector to receive fluid from a reservoir and having a first connector, a second connector, and a third connector, wherein the third connector is attachable to tubing to communicate with the reservoir and the first connector is to be connected to the open first end and the second connector is to be connected to the open second end to provide an annular elastic tube with an internal flow path that is continuous and annular around the annular elastic tube, wherein the first connector extends in a first direction and the second connector extends in a second direction and the first direction and the second direction define an angle relative to one another that is greater than 90 degrees and less than 180 degrees, such that the connector provides a non-linear curved fit against the urethra, and the elastic tube receives and dispatches the fluid to coapt the urethra for continence and open the urethra for voiding.

10. The system of claim 9, wherein one portion of the elastic tube is at least one of flattened out and oval shaped to be inserted behind the urethra.

11. The system of claim 9, wherein the elastic tube is pre-shaped into one of a circular shape and an oval shape for wrapping around the urethra.

12. The system of claim 9, wherein one of the first end and second end of the elastic tube is over-molded onto the corresponding one of the first connector and the second connector.

13. The system of claim 9, comprising a control device, wherein the third connector is adapted to be fluidically connected to the control device that regulates flow of the fluid to and from the connector.

14. The system of claim 13, wherein the control device includes a pump that transfers the fluid to one of the elastic tube to expand the elastic tube and the reservoir to deflate the elastic tube.

15. The system of claim 13, wherein the control device regulates the flow of the fluid between the reservoir and the elastic tube.

16. The system of claim 15, wherein the reservoir maintains an elevated fluid pressure and the control device regulates the flow of the fluid from the reservoir to the elastic tube to inflate the elastic tube.

17. The system of claim 9, wherein the elastic tube includes an elastomer.

18. An artificial urinary sphincter system, comprising:
an elastic tube to be wrapped around a urethra and having at least one connector, wherein the elastic tube has a first end that provides a first opening to receive and dispatch fluid, a second end that provides a second opening, and tubing between the first end and the second end, where the first end of the elastic tube is insertable into the second opening of the second end of the elastic tube to provide an annular elastic tube with an internal flow path that is continuous and annular around the annular elastic tube, such that the fluid can flow all the way around the annular elastic tube including from the second end into the first opening without flowing through the tubing between the first end and the second end; and
a reservoir to hold the fluid;
wherein the annular elastic tube receives and dispatches the fluid to expand and contract the annular elastic tube and to coapt the urethra for continence and open the urethra for voiding;
wherein the elastic tube is fluidically connected to a control device, and the control device regulates the flow of the fluid between the reservoir and the elastic tube.

* * * * *